United States Patent
Riley et al.

(10) Patent No.: US 8,519,209 B2
(45) Date of Patent: Aug. 27, 2013

(54) METHOD TO ADJUST 2-PHENYL CONTENT OF AN ALKYLATION PROCESS FOR THE PRODUCTION OF LINEAR ALKYL BENZENE

(71) Applicant: UOP LLC, Des Plaines, IL (US)

(72) Inventors: Mark G. Riley, Hinsdale, IL (US); Stephen W. Sohn, Arlington Heights, IL (US); Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/779,221

(22) Filed: Feb. 27, 2013

(65) Prior Publication Data

US 2013/0172646 A1    Jul. 4, 2013

Related U.S. Application Data

(62) Division of application No. 12/965,040, filed on Dec. 10, 2010, now Pat. No. 8,389,786.

(51) Int. Cl.
*C07C 2/66* (2006.01)
*C07C 6/12* (2006.01)

(52) U.S. Cl.
USPC ............ 585/323; 585/467; 585/455; 585/475

(58) Field of Classification Search
USPC ................... 585/323, 467, 455, 475
See application file for complete search history.

(56) References Cited

U.S. PATENT DOCUMENTS

2009/0062583 A1 * 3/2009 Guillon et al. ................ 585/301

* cited by examiner

*Primary Examiner* — Thuan D Dang
(74) *Attorney, Agent, or Firm* — Arthur E Gooding

(57) ABSTRACT

A process is presented for controlling the output of monoalkylated benzenes. The alkylbenzenes are linear alkylbenzenes and the process controls the 2-phenyl content of the product stream. The control of the process to generate a linear alkylbenzene with a 2-phenyl content within a desired range by recycling a portion of the effluent from the alkylation reactor to the inlet of the reactor.

1 Claim, No Drawings

METHOD TO ADJUST 2-PHENYL CONTENT OF AN ALKYLATION PROCESS FOR THE PRODUCTION OF LINEAR ALKYL BENZENE

CROSS-REFERENCE TO RELATED APPLICATION

This application is a Division of prior application Ser. No. 12/965,040 which was filed on Dec. 10, 2010, now U.S. Pat. No. 8,389,786 the contents of which are incorporated herein by reference thereto.

FIELD OF THE INVENTION

The field of the invention is benzene alkylation, with a more particular area of the control of the production of linear alkyl benzene.

BACKGROUND OF THE INVENTION

The alkylation of aromatic hydrocarbons such as benzene is a well-developed art, and one that is practiced commercially using solid catalysts in large scale industrial units. Two common commercial applications are the production of ethyl benzene and cumene (isopropyl benzene). The production of ethyl benzene is the process of alkylating benzene with ethylene to produce ethyl benzene, which is the precursor used in the production of styrene. The production of cumene is the process of alkylating benzene with propylene to form isopropylbenzene, and which is used in the production of phenol. The production of ethyl benzene and cumene have undergone continual improvement, and an example of the process and typical flow scheme is shown in U.S. Pat. No. 4,051,191.

The performance of alkylation processes is controlled by the activity and selectivity of the catalyst in the process operating environment. Catalysts used in the alkylation process are solids that have considerable acidity, such as aluminum chloride and zeolites. However, there is considerable expense associated with the loading of large quantities of catalyst into a commercial reactor. Due to the nature of aromatic alkylation catalyst deactivation, the initial catalyst loadings in commercial fixed-bed operations generally contain far more catalyst than is needed at any given time to catalyze the alkylation reaction. Only a small portion of the active catalyst sites in fresh catalyst loadings is utilized for the desired alkylation reaction, while catalyst beyond the easily recognizable alkylation exotherm is essentially not used for alkylation initially. Moreover, the active acid sites in this downstream portion of the catalyst bed tend to promote undesirable side reactions, such as the formation of oligomers and diphenyl alkanes.

The use of larger alkyl groups in the production of alkylbenzene is important for the manufacture of detergents. About thirty years ago it became apparent that household laundry detergents made of heavily branched alkylbenzene sulfonates were gradually polluting rivers and lakes. Solution of the problem led to the manufacture of detergents made of linear alkylbenzene sulfonates (LABS). The alkylbenzenes with alkyl groups that are linear biodegrade more quickly than alkylbenzenes with branched alkyl groups. It became very desirable to produce relatively pure linear alkyl benzenes for the production of detergents.

However, the chemistry is complex, and the alkyl groups are often a complex mix of isomers, as well as undergoing isomerization during the processes used in the production of linear alkyl benzenes. Control of the alkylation process to produce a product meeting purity specifications is important for the quality of the final product, or LABS.

SUMMARY OF THE INVENTION

Alkylaromatics are important for the production of detergents. The structure of the alkylaromatic compounds, and in particular, the 2-phenyl content of the alkylaromatic compounds is important to the quality of the product. The present invention is a process for controlling the 2-phenyl content in the benzene alkylation process. The process includes passing a benzene stream and a linear olefin stream to an alkylation reactor. The benzene and olefins are reacted over an alkylation catalyst at reaction conditions to generate an effluent stream comprising a linear alkylbenzene, with the alkylbenzene having a 2-phenyl content. The 2-phenyl content of the alkylbenzene in the effluent stream is measured. A portion of the effluent stream is passed to the reactor inlet to adjust the benzene to olefin ratio of the feed streams. The measured 2-phenyl content of the alkylbenzene in the effluent stream is used to control the size of the portion of the effluent stream recycled to the inlet of the reactor.

In one embodiment, the effluent stream can be separated into a first stream having a relatively rich concentration of benzene, and a second stream having a relatively lean concentration of benzene. A portion of the first stream is then recycled to the reactor inlet in response to the measured 2-phenyl content of the alkylbenzenes in the effluent stream. The separation can be a rough separation to limit the amount of energy expended in creating the stream relatively enriched with benzene.

Other objects, advantages and applications of the present invention will become apparent to those skilled in the art from the following detailed description.

DETAILED DESCRIPTION OF THE INVENTION

The present invention provides a process for the control of 2-phenyl content in the process for the production of linear alkylbenzenes. The alkylation of benzene is performed with an acidic catalyst. The activity of the acidic catalyst decreases over time, and the quality of the effluent from an alkylation reactor also decreases over time. In the past, maintaining the quality has been through constant operation of the process, and when the quality fell below an acceptable level, the catalyst was regenerated to return the process to generating a product of acceptable purity levels. The alkylation process generally uses a fixed bed, and with a fixed bed process, the reactor bed is regenerated off-line, while a second reactor bed is brought on line to continue the process.

In the alkylation of aromatics, one of the major variables in the process is the molar ratio of the aromatic compound to the alkylating compound, or the benzene to olefin ratio. This process variable, the benzene to olefin molar ratio, impacts the ratio of monoalkylate to polyalkylate. The ratio is usually kept high to limit the production of dialkylated benzene, or trialkylated benzene. However, it has been unexpectedly found that the benzene to olefin ratio also impacts other aspects of the alkylated benzene product.

Control of the benzene to olefin ratio also impacts the position on the olefin compound where benzene attaches. This impacts the 2-phenyl content of detergent range linear alkylbenzene (LAB). The 2-phenyl content of detergent range LAB is an important product specification and can be partially controlled by controlling the benzene to olefin ratio.

The 2-phenyl content of a monoalkylbenzene product stream is calculated by dividing the weight of the 2-pheny linear monoalkylbenzene in the stream by the weight of the stream, or the content is the weight percent. Consider a stream comprised of linear phenyloctanes. Due to normal issues when fractionating mixtures of a large number of compounds, such as close boiling points and fractionation inefficiencies, the monoalkylate stream will include isomers such as branched phenyloctanes and small amounts of heavy alkylate such as dioctylbenzenes. The normal fractionation generally produces an overhead stream of monoalkylate and a bottoms stream of heavy alkylate. For example, if one considers a stream of linear phenyloctanes, the linear mono alkylbenzenes include 2-phenyloctane, 3-phenyloctane and 4-phenyloctane. The 1-phenyloctane isomer is not produced in any significant amount. The 2-phenyl content will then be the mass of the 2-phenyloctane divided by the total mass of the linear phenyloctanes, branched phenyloctanes and heavy alkylate in the product stream. Increasing the alkyl chain length increases the number of isomers. A catalyst that shows equal probability of alkylating at any internal olefin position would therefore reduce the 2-phenyl content as the chain length increases.

Linear alkylbenzenes having between 8 and 16 carbon atoms in the alkyl chain are commercially valuable as precursors for detergents and surfactants. Preferably, the alkyl chains are in the range of 10 to 13 carbon atoms. The 2-phenyl content has an impact of a number of performance properties of sodium linear alkylbenzene sulfonate salt, such as the solubility and viscosity. The 2-phenyl content is a specification that detergent manufacturers set, and 2-phenyl content outside the specification has low market value. The present invention provides a means to achieve a desired 2-phenyl content for the linear alkylbenzene product.

The production of linear alkylbenzenes has traditionally been made in two commercial forms, low 2-phenyl and high 2-phenyl. Low 2-phenyl LAB is made by HF alkylation and results in a 2-phenyl concentration between 15 and 20 mass percent of the LAB. This is due to the homogeneous acid, HF, lack of preference for catalyzing the attachment of the benzene to the olefin chain. There is not alkylation on the terminal carbons, and the internal carbons have a nearly equal probability of alkylation, and which produces shorter chained alkyl groups extending from the benzene. High 2-phenyl LAB has been historically made using $AlCl_3$ alkylation, but is also produced with other solid alkylation catalysts, and results in a 2-phenyl concentration between 15 and 45 mass percent of the LAB. A preferred range for the 2-phenyl concentration is between 20 and 35 mass percent.

Adding fresh benzene is an expensive proposition because of the energy required to produce a benzene stream that has had impurities removed. However, it has been found that molecular sieve catalysts, such as zeolites, can use much lower benzene to olefin ratios as the catalysts inhibit the formation of polyalkylbenzenes. The present invention makes use of this to utilize an inexpensive source of benzene. The benzene in the effluent stream from the alkylation reactor can be recycled back to the reactor inlet, without separation of effluent products from the effluent stream.

The present invention is a process for controlling the 2-phenyl content in the benzene alkylation process. The process includes passing a benzene stream and a linear olefin stream to an alkylation reactor, and reacting the linear olefin with the benzene over a catalyst to produce an effluent stream comprising benzene and alkylbenzene. The 2-phenyl content of the alkylbenzene in the effluent stream is measured. A portion of the effluent stream is passed to the reactor inlet in response to the 2-phenyl content in the effluent stream. The benzene in the effluent stream is used to control the benzene to olefin ratio in the reactor feed. Although the effluent stream includes LAB, the increase in polyalkylbenzene is very small. The 2-phenyl content of the alkylbenzene is between 15% and 45% by mass of the alkylbenzene produced. The preferred 2-phenyl content of the alkylbenzene is between 20% and 35% by mass of the alkylbenzene produced.

In one embodiment, the process can make a rough separation of the effluent stream. The effluent stream is separated into a first stream comprising alkylbenzenes and a second stream comprising benzene. The second stream is then passed to the alkylation reactor inlet to increase the benzene to olefin ratio in the reactor feed. The separation process is not intended to produce a pure, or relatively pure, stream of benzene, but to create the first stream that is relatively rich in alkylbenzenes and the second stream relatively depleted in alkylbenzenes. An example would be a distillation column with only a few trays, such as 5 or less, where the bottoms stream will have a relatively reduced benzene content, and the overhead stream will have a relatively increased benzene content. A flash separation would also be a sufficient rough separation to provide an overhead stream having a relative increase in benzene concentration. The process of separation will create a second, or benzene, stream with an increased temperature. The benzene stream can be passed through a heat exchanger to adjust the temperature of the benzene stream before passing the benzene stream to the reactor inlet. The heat exchanger can also recover some of the energy put into the rough cut separation of the effluent stream.

In an embodiment, the process can further include passing the first stream having alkylbenzenes to a separation unit. The separation unit generates a third stream comprising monoalkylated benzene and a fourth stream comprising polyalkylated benzene. The polyalkylated benzene stream is then passed to a trans-alkylation reactor. A benzene stream is also passed to the trans-alkylation reactor where the benzene and polyalkylated benzene react over a trans-alkylation catalyst at trans-alkylation reaction conditions to form an effluent stream having benzene, monoalkylated benzene and a reduced amount of polyalkylated benzene.

A portion of the second stream, or overhead benzene stream, from the rough separation can be passed to the transalkylation reactor to provide additional benzene in the transalkylation process.

The use of solid alkylation catalysts can include a mixture of two or more solid alkylation catalysts. The use of two or more catalysts allows for catalysts with different acidic components and different catalytic activities. In addition, different catalysts have different rates of decline in their activities. Therefore, control in the alkylation process can be influenced by adjusting flow rates of the reactants to the effluent stream, as the effluent stream changes due to the changing activities of the catalysts. In one embodiment, the present invention can use two catalytic materials. When two catalytic materials are used, the first catalytic material can comprise a faujasite having a rare earth metal deposited thereon. The second catalytic material is a zeolitic material and is chosen from the group of zeolites having UZM-8, MWW, BEA, OFF, MOR, LTL, or MTW type structures.

In another embodiment, the invention is a process for controlling the 2-phenyl content of monoalkylated benzene. The process includes passing a benzene stream and a linear olefin stream to an alkylation reactor. The linear olefin and benzene react over a catalyst at reaction conditions to produce an effluent stream comprising benzene and alkylbenzenes. A portion of the effluent stream is used as a recycle stream and is passed to the inlet of the alkylation reactor. The recycling of a portion of the effluent stream to the reactor inlet increases the benzene to olefin ratio of the reactor feed. The 2-phenyl content of the alkylbenzenes in the effluent stream is measured, and used to control the amount of recycle to the reactor inlet. The control of the recycle controls the benzene to olefin ratio, and in turn controls the 2-phenyl content of the effluent stream. The control is set to preset limits for a desired 2-phenyl content that is between the preset limits.

The process can further include passing the effluent stream to a separation unit. The separation unit generates a first stream comprising benzene, a second stream comprising monoalkylbenzene and a third stream comprising heavies which include polyalkylbenzenes. The separation unit can comprises two columns, a benzene column and a monoalkylbenzene column, where the benzene is removed from the effluent stream in the benzene column, and the monoalkylbenzene is separated from the heavies in the monoalkylbenzene column. The third stream, having polyalkylbenzenes and in particular dialkylbenzene, is passed to a transalkylation reactor. The benzene recovered from the benzene column can be used in the alkylation column or the transalkylation column. A portion of the first stream is passed to the alkylation reactor in response to the measurement of the 2-phenyl content in the effluent stream.

Alkylation reaction conditions include a temperature between 50° C. to 200° C., and preferably between 80° C. to 175° C. The pressures in the reactor are from 1.4 MPa (203 psia) to 7 MPa (1015 psia), and preferably from 2 MPa (290 psia) to 3.5 MPa (507 psia). The pressures and temperatures are adjusted to maintain the reaction in the liquid phase. To minimize polyalkylation of the benzene, the aryl to monoolefin molar ratio is between 2.5:1 to 50:1, and preferably between 5:1 to 35:1. The average residence time in the reactor helps control product quality, and the process is operated at a liquid hourly space velocity (LHSV) from 0.1 to 30 $hr^{-1}$, with a preferred LHSV between 0.3 to 6 $hr^{-1}$.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for controlling the 2-phenyl content in the benzene alkylation process, comprising:
    passing a benzene stream to an alkylation reactor;
    passing a linear olefin to the alkylation reactor wherein the olefin comprises olefins having from 8 to 16 carbon atoms;
    reacting the linear olefin with the benzene over a catalyst comprising two catalytic materials to produce an effluent stream comprising benzene and alkylbenzene, wherein the first catalytic material comprises a faujasite having a rare-earth metal deposited thereon, and the second catalytic material is UZM-8;
    measuring the 2-phenyl content of the alkylbenzene in the effluent stream;
        passing a portion of the effluent stream to the alkylation reactor to increase the benzene to olefin ratio of the feed; and
    passing the effluent stream to a separation unit to generate a first stream comprising benzene, a second stream comprising monoalkylbenzene, and a third stream comprising polyalkylbenzene;
        controlling the benzene to olefin ratio in the feed through control of the portion of the second stream to the reactor in response to the 2-phenyl content, wherein the desired 2-phenyl content is between preset limits;
    passing the third stream and a portion of the first stream to a transalkylation reactor; and
    passing a portion of the first stream to the alkylation reactor in response to the 2-phenyl content of the effluent stream.

* * * * *